United States Patent
Al Anezi

(10) Patent No.: US 11,219,415 B1
(45) Date of Patent: *Jan. 11, 2022

(54) THERMAL IMAGING SYSTEM FOR DISEASE OUTBREAK DETECTION

(71) Applicant: Prince Mohammad Bin Fahd University, Dhahran (SA)

(72) Inventor: Faisal Al Anezi, Dhahran (SA)

(73) Assignee: Prince Mohammad Bin Fahd University, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/346,920

(22) Filed: Jun. 14, 2021

Related U.S. Application Data

(63) Continuation of application No. 17/014,288, filed on Sep. 8, 2020, now Pat. No. 11,064,953.

(60) Provisional application No. 63/062,813, filed on Aug. 7, 2020.

(51) Int. Cl.
*G16H 50/80* (2018.01)
*A61B 5/00* (2006.01)
*G01K 13/20* (2021.01)
*G16H 50/20* (2018.01)

(52) U.S. Cl.
CPC .......... *A61B 5/7282* (2013.01); *A61B 5/0008* (2013.01); *G01K 13/223* (2021.01); *G16H 50/20* (2018.01); *G16H 50/80* (2018.01)

(58) Field of Classification Search
CPC .................................................... G16H 50/80
See application file for complete search history.

(56) References Cited

U.S. PATENT DOCUMENTS

| | | | |
|---|---|---|---|
| 7,447,333 B1 | 11/2008 | Masticola et al. |
| 8,519,850 B2 | 8/2013 | Reinpoldt |
| 9,536,355 B1 | 1/2017 | Kumar et al. |
| 2015/0302654 A1 | 10/2015 | Arbouzov |
| 2017/0344833 A1 | 11/2017 | Ahlberg |
| 2018/0046778 A1 | 2/2018 | Jiang |
| 2018/0058939 A1 | 3/2018 | Pompei et al. |

(Continued)

OTHER PUBLICATIONS

Claude Hochreutiner, "How smarter AI-powered cameras can mitigate the spread of Wuhan Novel Coronavirus (COVID-19), and what we've learned from the SARS outbreak 17 years prior", Anyconnect, https://anyconnect.com/blog/smart-thermal-cameras-wuhan-coronavirus, Jan. 31, 2020, 23 pages.

(Continued)

*Primary Examiner* — Mallika D Fairchild
*Assistant Examiner* — Nathan A Baldwin
(74) *Attorney, Agent, or Firm* — Oblon, McClelland, Maier & Neustadt, L.L.P.

(57) ABSTRACT

A fever-causing disease outbreak detection system for an early warning of the outbreak of an infectious disease. The system uses an array of infrared detectors to measure the temperatures of individuals in a population. The measured temperatures are used to create a measured population temperature distribution. A central control unit generates a predicted population temperature distribution using environmental data such as local atmospheric conditions and compares the predicted population temperature distribution to the measured population temperature distribution. If an outbreak is detected, an alert is issued.

8 Claims, 10 Drawing Sheets

(56) References Cited

U.S. PATENT DOCUMENTS

| | | | |
|---|---|---|---|
| 2018/0064349 A1* | 3/2018 | Kerr | A61B 5/01 |
| 2018/0110416 A1 | 4/2018 | Masuda et al. | |
| 2019/0053470 A1* | 2/2019 | Singh | A01K 11/006 |
| 2019/0019201 A1 | 6/2019 | Mane | |
| 2019/0192010 A1* | 6/2019 | Mane | G16H 50/30 |
| 2019/0287682 A1* | 9/2019 | Van Zon | G16H 40/20 |
| 2020/0146557 A1 | 5/2020 | Cheung et al. | |
| 2021/0304406 A1* | 9/2021 | Starr | G06F 3/017 |

OTHER PUBLICATIONS

"China uses AI to combat the novel coronavirus outbreak", Tsinghua University/Megvii, https://healthcare-in-europe.com/en/news/china-uses-ai-to-combat-the-novel-coronavirus-outbreak.html, Feb. 18, 2020, 3 pages.

R. James Seffrin, "Thermal Imaging for Detecting Potential SARS Infection", irinfo.org, National Conference on Thermal Imagers for Fever Screening—Selection, Usage and Testing, https://irinfo.org/06-01-2003-seffrin/, May 30, 2003, 11 pages.

Angela Noufaily, et al., "Comparison of statistical algorithms for daily syndromic surveillance aberration detection", Bioinformatics, vol. 35, No. 17, 2019, 3110-3118.

Piotr dollár, et al., "Pedestrian Detection: An Evaluation of the State of the Art", Submission To IEEE Transactions on Pattern Analysis and Machine Intelligence, vol. 34, Issue 4, Aug. 4, 2011, pp. 743-761.

Deep Learning. Investopedia, Investopedia, Jan. 22, 2019, www.investopedia.com/terms/d/deep-learning.asp (Year: 2019).

\* cited by examiner

THERMAL IMAGING SYSTEM FOR DISEASE OUTBREAK DETECTION

CROSS-REFERENCE TO RELATED APPLICATIONS

The present application is a Continuation of U.S. application Ser. No. 17/014,288, now allowed, having a filing date of Sep. 8, 2020 which claims priority to U.S. Provisional Application No. 63/062,813, having a filing date of Aug. 7, 2020 which is incorporated herein by reference in its entirety.

BACKGROUND OF THE INVENTION

Field of the Invention

The present disclosure relates to an automated fever-causing disease outbreak detection and alert system.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Infectious diseases pose great risk to the health of people in countries around the globe. The ability for the infectious disease to spread throughout a population raises the possibility of widespread illness, overwhelming of healthcare facilities, severe economic disruption, and even large numbers of deaths. For example, in November 2002 through July 2003, a total of 8,422 people contracted a previously-unknown respiratory infectious disease called "sudden acute respiratory syndrome" (SARS) [Chan-Yeung, M. & Xu, R.H., Respirology, 2003, 8, S9-S14]. In April 2009 through April 2010, an estimated 60.8 million cases of a strain of influenza known as H1N1 were in the United States alone, resulting in approximately 12,500 deaths [Shrestha, S. S., et. al., Clinical Infectious Diseases, 2011, 52, Suppl. 1, S75-S82]. In February 1957 through fall 1957, an estimated 1.1 million deaths were caused by a different strain of influenza known as H2N2 [Viboud, C., et. al., The Journal of Infectious Diseases, 2016, 213, 5, 738-745]. The risks and devastating consequences of such outbreaks cannot be overstated. Global healthcare experts at agencies such as the CDC and WHO devote millions of dollars and thousands of man-hours each year to the detection and prevention of such outbreaks. Rapid detection and identification of an outbreak of such a disease can be used by such experts to halt the spread and contain such outbreaks before widespread infection can occur.

A promising method of outbreak detection and identification is syndromic surveillance. Syndromic surveillance is a method for finding individuals who may have an infectious disease by monitoring a population for individuals who display outward, detectable symptoms of the disease, e.g. fever, coughing, and/or sneezing. While not all infectious diseases present symptoms that are easily detectable by syndromic surveillance methods, there are many of dramatic global health importance which do. Of outward symptoms, fever is particularly useful in syndromic surveillance. This is due mainly because of the relative ease with which it may be detected. Simply taking an individual's temperature is typically sufficient for fever detection.

Traditionally, syndromic has been performed by manual reporting by healthcare workers. This approach, however, has many drawbacks such as late detection due to the patient seeking medical care only when symptoms become severe, missing patients who die before care can be given and symptoms recorded, and patients not being counted due to lack of access to healthcare. Recently, more technologically sophisticated methods and systems have been developed. For example, US20170344833A1 discloses a method and system for identifying an individual with increased body temperature. The method and system are used to identify and track individuals who exhibit what may be a fever to allow for isolation and treatment of said individuals using visual and infrared images. Additionally, U.S. Pat. No. 7,447,333B1 discloses a method and system of syndromic surveillance which combines fever detection and coughing/sneezing detection to identify and track individuals which may be infected with an infectious disease. While these methods and systems are useful in tracking individual persons who may be in need of isolation or medical care, they lack population-level detection and/or analysis capabilities which are necessary in an infectious disease outbreak detection system. No assessment of factors such as the total number or percentage of suspected infections in a population, the geographic location of a suspected outbreak, or the ability to discriminate a background level of non-epidemic or non-epidemic diseases from dangerous epidemic or pandemic outbreaks can be made by such systems which lack population-level analysis. The systems described above may be useful in helping combat the spread of an infectious disease by allowing for isolation of and medical attention be provided to sick individuals, but these systems are useful only after the infectious disease outbreak is known. The systems and methods lack critical early warning capabilities.

In view of the forgoing, one object of the present disclosure is to provide an automated system for the detection of an outbreak of a fever-causing disease. The automated system has early warning capabilities that allow for alerting health authorities by the detection of disease outbreaks. Such outbreaks are detected using population-level collection and analysis of syndromic data, including body temperature.

SUMMARY OF THE INVENTION

The present disclosure relates to a fever-causing disease outbreak detection system comprising a central control unit comprising a wireless connection device, a measurement processing unit, a prediction generating unit, and an alert output device; and an array of infrared detectors wirelessly connected to the central control unit, wherein the array of infrared detectors measures temperatures of persons in a measured population; and the central control unit receives measured data comprising the temperatures of persons in the measured population via the wireless connection device, processes the temperatures using the measurement processing unit to form a measured population temperature distribution, generates a predicted population temperature distribution using the prediction generating unit, compares the measured population temperature distribution to the predicted population temperature distribution to determine an outbreak condition, and issues an alert if the outbreak condition meets an alert criterion using the alert output device.

In some embodiments, the central control unit further comprises an environmental data collection unit which receives environmental data corresponding to at least one selected from the group consisting of ambient temperature, ambient temperature history, room temperature, room temperature history, local atmospheric temperature, local atmospheric temperature history, humidity, humidity history, time of day, time of year, secondary location temperature, and secondary location temperature history.

In some embodiments, the prediction generating unit generates the predicted population temperature distribution using the environmental data.

In some embodiments, the prediction generating unit generates the predicted population temperature distribution using a machine learning algorithm or model.

In some embodiments, the machine learning algorithm or model is an artificial neural network.

In some embodiments, the infrared detectors are selected from the group consisting of mounted thermal imaging cameras, handheld thermal imaging cameras, wearable thermal imaging cameras, and smart thermometers; and are connected to the central control unit via an internet connection.

In some embodiments, the measured data comprising the temperatures of persons in the measured population is in the form of thermal images comprising one or more persons.

In some embodiments, the fever-causing disease outbreak detection system further comprises an image processor which processes the thermal images so as to obtain the temperatures of persons in the measured population.

In some embodiments, the array of infrared detectors or the central control unit transmit thermal images to an external image processor which is not part of the system, then the central control unit receives from the external image processor the temperatures of persons in the measured population.

In some embodiments, the system is capable of identifying and tracking individuals in the measured population temperature distribution likely exhibiting a fever.

In some embodiments, the array of infrared detectors is distributed across and measures the temperatures of persons within population centers selected from the group consisting of transit facilities such as airports, train stations, metro stations, and bus stations or depots; healthcare facilities such as hospitals and clinics; commercial centers such as shopping malls, markets, food courts or food halls, and amusement parks; public parks; residential facilities such as apartment buildings, condominium buildings, and neighborhoods; and work facilities such as office buildings and factories.

The present disclosure also relates to a method of detecting a fever-causing disease outbreak comprising measuring temperatures of persons in a measured population using an array of infrared detectors, receiving via an internet connection the temperatures at a central control unit, processing the temperatures to form a measured population temperature distribution, generating a predicted population temperature distribution, comparing the measured population temperature distribution to the predicted population temperature distribution to determine an outbreak condition, and optionally issuing an alert if the outbreak condition meets an alert criterion.

In some embodiments, the measuring is performed with one or more infrared detectors selected from the group consisting of mounted thermal imaging cameras, handheld thermal imaging cameras, wearable thermal imaging cameras, and smart thermometers.

In some embodiments, the measuring comprises obtaining one or more thermal images, and extracting from the thermal images the temperatures of persons depicted in the images.

In some embodiments, the generating is performed using a machine learning algorithm or model.

In some embodiments, the machine learning algorithm or model is an artificial neutral network.

In some embodiments, the method further comprises collecting environmental data corresponding to at least one selected from the group consisting of ambient temperature, ambient temperature history, room temperature, room temperature history, local atmospheric temperature, local atmospheric temperature history, humidity, humidity history, time of day, time of year, secondary location temperature, and secondary location temperature history.

In some embodiments, the method further comprises identifying and tracking individuals in the measured population temperature distribution likely exhibiting a fever.

The present disclosure also relates to a non-transitory processor readable medium having processor instructions that are executable to cause a processor to generate a predicted population temperature distribution using a machine learning algorithm or model, generate a measured population temperature distribution using a plurality of measured temperatures of persons, compare the measured population temperature distribution to the predicted population temperature distribution, and issue an alert-generating output if the comparing meets an alert criterion.

In some embodiments, the predicted population temperature distribution is generated with at least one additional input data selected from the group consisting of ambient temperature, ambient temperature history, room temperature, room temperature history, local atmospheric temperature, local atmospheric temperature history, humidity, humidity history, time of day, time of year, secondary location temperature, and secondary location temperature history.

DETAILED DESCRIPTION OF THE INVENTION

In the following description, it is understood that other embodiments may be utilized and structural and operational changes may be made without departure from the scope of the present embodiments disclosed herein.

As used herein, the terms "optional" or "optionally" means that the subsequently described event(s) can or cannot occur or the subsequently described component(s) may or may not be present.

Fever-Causing Disease Outbreak Detection System

Figure 1:
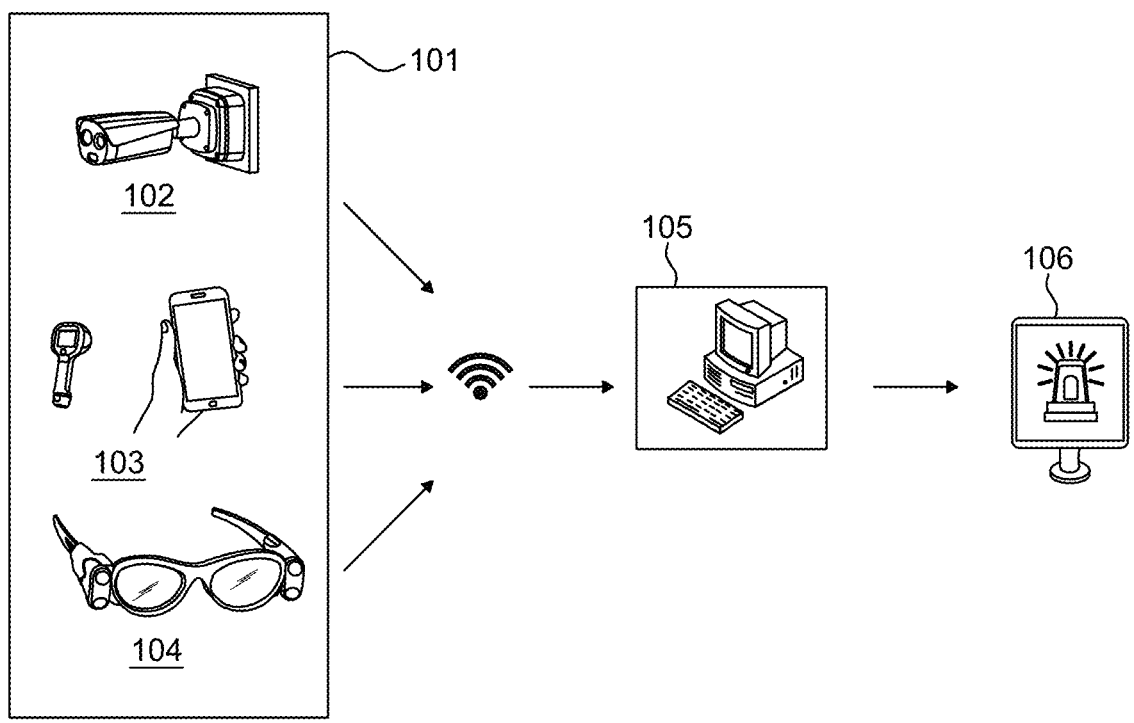
FIG. 1 is a representation of components of the fever-causing disease outbreak detection system.

According to a first aspect, the present disclosure relates to a fever-causing disease outbreak detection system. This system comprises a central control unit and an array of infrared detectors wirelessly connected to the central control unit. The central control unit comprises a wireless connection device, a measurement processing unit, a prediction generating unit, and an alert output device. FIG. 1 is a representation of components of the fever-causing disease outbreak detection system showing the array of infrared detectors (101) showing mounted thermal imaging cameras (102), handheld thermal imaging cameras (103), and wearable thermal imaging cameras (104), the array being wirelessly connected to the central control unit (105), and an alert output by the alert output device (106).

The central control unit receives measured data comprising the temperatures of persons in the measured population via the wireless connection device, processes the temperatures using the measurement processing unit to form a measured population temperature distribution, generates a predicted population temperature distribution using the prediction generating unit, compares the measured population temperature distribution to the predicted population temperature distribution to determine an outbreak condition, and issues an alert if the outbreak condition meets an alert criterion using the alert output device.

The use of population-level analysis may be advantageous for accurate detection of an outbreak condition. One example of an advantage that such population-level analysis may impart is a reduction in false positives, situations in which an outbreak has not occurred or is not currently occurring. These false positives may be triggered in other systems by individuals who have an elevated body temperature but are not exhibiting a fever. Some examples of situations which may cause an individual to have an elevated body temperature in the absence of a fever include, but are not limited to individuals who are actively exercising, have recently exercised, have hurried to catch a train, plane, bus, or other means of transport, was recently in a hot environment, is late for an appointment, is exhibiting nervousness or stress, has a non-fever medical condition which causes an elevated body temperature, and individuals who have a normal body temperature above about 98.6° F. For an illustrative example that highlights the aforementioned advantages, consider an embodiment where the system is in an airport. In a situation where an individual has to run through the airport to catch an imminently departing flight, that individual would exhibit an elevated body temperature. An outbreak alert issued based on this individual's elevated body temperature would be a false alarm and potentially waste precious resources necessary to combat an outbreak of a fever-causing disease. Alternatively, in a large population of people, it is statistically possible that a small percentage of individuals in said population have a fever not related to an outbreak of a fever-causing disease. The population-level analysis of the current invention can be configured to account for a normal, base level of individuals exhibiting a fever to more accurately detect specific outbreaks that require specific or abnormal responses. Such configuration may be accomplished by, for example, manual or automatic adjustment of the alter criterion.

In some embodiments, the central control unit further comprises an environmental data collection unit which receives environmental data corresponding to at least one selected from the group consisting of ambient temperature, ambient temperature history, room temperature, room temperature history, local atmospheric temperature, local atmospheric temperature history, humidity, humidity history, time of day, time of year, secondary location temperature, and secondary location temperature history. The inclusion of such environmental data may be advantageous for the generation of the predicted population temperature distribution or in comparing the predicted and measured population temperature distributions, or both. In some embodiments, the prediction generating unit generates the predicted population temperature distribution using the environmental data. The use of such environmental data in generating the predicted population temperature distribution may be advantageous in allowing the predicted population temperature distribution to account for changes in a population temperature distribution caused by factors such as seasonal changes, time of day, and local atmospheric conditions. The local atmospheric conditions can have an impact on an individual's temperature. For example, a person who had recently come inside from a sunny, hot day outside would have an elevated body temperature compared to someone who had been sedentary in a cool interior space over the same time period, even in the absence of a fever. The environmental data described above allows the system to, among other things, account for these local atmospheric conditions in the predicted population temperature distribution.

In some embodiments, the environmental data is accessed and/or compiled from a weather data database or repository. Such databases or repositories are typically collected and updated by national or international agencies. Examples of such agencies include, but are not limited to the US National Oceanographic and Atmospheric Agency (NOAA), the US National Weather Service, the US National Aeronautics and Space Administration (NASA), the World Meteorological Organization, the European Center for Medium-Range Weather Forecasting (ECMWF), the European Organization for the Exploitation of Meteorological Satellites (EUMETSAT) the Trans-African HydroMeteorological Observatory (TAHMO), the African Centre of Meteorological Application for Development (ACMAD), the European Space Agency, the India Meteorological Department, the Australian Bureau of Meteorology, the China Meteorological Administration, the UK Met Office, the Meteorological Service of Canada, the Deutscher Wetterdienst, the South African Weather Service, and the Presidency of Meteorology and Environment of Saudi Arabia. Similar databases or repositories may be collected and updated by private entities. Some databases or repositories run by private entities collect or compile weather data from national or international agencies. In some embodiments, the weather data database or repository is accessed and/or compiled via a wireless or wired internet connection.

In some embodiments, the environmental data is accessed and/or compiled from an environmental observation system. In some embodiments, the environmental observation system comprises a group of interior space sensors and/or atmospheric sensors. The group of interior space sensors preferably comprises at least one interior temperature sensor. The interior temperature sensor may be any suitable sensor known to one of ordinary skill in the art. Examples of such interior temperature sensors are thermometers, bimetallic mechanical or electrical sensors, electronic thermistors and semiconductor devices, and electrical thermocouples. In some embodiments, the interior temperature sensor is part of a heating, ventilation, and air conditioning (HVAC) system. The group of atmospheric sensors preferably comprises atmospheric sensors which collect multiple atmospheric data types, such as humidity, temperature, and atmospheric pressure. The atmospheric sensors may be any suitable atmospheric sensor known to one of ordinary skill in the art. Examples of such atmospheric sensors are thermometer for measuring air and sea surface temperature, barometer for measuring atmospheric pressure, hygrometer for measuring humidity, anemometer for measuring wind speed, pyranometer for measuring solar radiation, rain gauge for measuring liquid precipitation over a set period of time, wind sock for measuring general wind speed and wind direction, wind vane (also called a weather vane or a weathercock) for determining wind direction, precipitation identification sensor for identifying falling precipitation, disdrometer for measuring precipitation drop size distribution, transmissometer for measuring visibility, and ceilometer for measuring cloud ceiling. In some embodiments, the environmental observation system includes a thermal image calibration target or reference. A thermal image calibration target or reference is an object which is either maintained at a known temperature or the temperature of which is closely monitored that is imaged in order to calibrate the output of a thermal imaging device. Such references may be out of frame (e.g., incorporated into the camera), or in frame (e.g., captured within the frame of view of the acquired image. The thermal image calibration target may be imaged alone or along with other objects. The thermal image calibration target may be imaged before, during, or after a thermal image is taken which contains objects of unknown temperature as part of measuring the temperature of said objects via thermal imaging. In some embodiments, the environmental data is accessed and/or compiled from the environmental observation system by a wireless connection. In some embodiments, the environmental data is accessed and/or compiled from the environmental observation system by a wired connection.

In some embodiments, the prediction generating unit generates the predicted population temperature distribution using a machine learning algorithm or model. As used herein, a machine learning algorithm refers to a procedure that is implemented on one or more training datasets that produces as an output a mathematical model useful in making predictions or decisions which involve data of the same identity as the data in the training datasets (e.g. temperatures, times, locations, etc.) without explicit instructions on the details of the model to be constructed and having the ability to modify the model without explicit instructions on which modifications to make. Machine learning algorithms have defined instructions on the type of model to generate and the procedure used to construct and refine said model, but the mathematical details of the model are determined automatically (i.e. without explicit programming instructions on said details) by a machine. Examples of machine learning algorithms include feature learning, sparse dictionary learning, anomaly detection, reinforcement learning, topic modeling, dimensionality reduction, deep learning, linear regression, logistic regression, decision trees, support vector networks (also known as support vector machines), k-nearest neighbors, k-means, Bayesian networks, genetic algorithms, and artificial neural networks (also known as neutral networks). The output of a machine learning algorithm is sometimes known as a machine learning model. As used herein, a machine learning model refers to a mathematical model useful for making predictions or decisions given input data wherein the model is generated and/or modified automatically (i.e. without explicit programming instructions on the details of the model or changes to the model) by a machine learning algorithm. Sometimes, the terms "machine learning algorithm" and "machine learning model" are used interchangeably, whether purposefully or mistakenly.

In some embodiments, the machine learning algorithm or model is an artificial neural network. A neural network is a type of machine learning algorithm or model which uses an interconnected group of nodes which receive node inputs, perform one or more calculations, and provide node outputs. The details of the calculation(s) performed by the nodes are provided by a process known as training in which a training dataset is provided to a neural network algorithm, the training dataset containing parameters which may or may not affect an outcome along with a corresponding outcome. The neural network algorithm generates a neural network model comprising nodes and weighted connections between nodes that is refined by the algorithm to correlate the parameters in the training dataset with the corresponding outcome in the training dataset. While the details of the calculation(s) performed by the nodes are determined during training, the nodes themselves provide a node output related to a node input by a mathematical relationship known as an activation function. The activation function determines the node output based on one or more node inputs. Examples of activation functions are linear, sigmoid, identity, binary step, Tan H, rectified linear unit, Gaussian error linear unit, SoftPlus, exponential linear unit, leaky rectified linear unit, ArcTan, square nonlinearity, bent identity, and sinusoid. Typically, the nodes are arranged in layers. A neural network commonly comprises at least three layers: an input layer, one or more hidden layers, and an output layer. The nodes of the input layer receive, compile, aggregate, access, or otherwise obtain input data from one or more data sources outside of the neural network and pass or transmit said input data to nodes of a first hidden layer. Typically, no computation is performed in the input layer. The nodes of the first hidden layer receive the input data from the input layer via weighted connections and perform a calculation using said input data. A hidden layer node may receive input data from one or more input nodes. A hidden layer node may have internal data, which is contained within the neural network that is also used in the calculation performed by the hidden layer node. This internal data is referred to as "bias". Sometimes, the bias is depicted as an additional input via a weighted connection to the hidden layer node which does not originate from an input layer node. The hidden layer node provides a computed data as an output. The computed data may be output to a second hidden layer or to an output layer. The second hidden layer functions similarly to the first hidden layer, receiving as inputs the computed data output from the first hidden layer via weighted connections and in turn providing further computed data as output. Such a structure may be repeated a desired number of times with additional hidden layers to achieve a desired result, the number of hidden layers being referred to as the "depth" of the neural network. The structure may form cycles, in which computed data from a given hidden layer is fed into a previous hidden layer which eventually is input into the given hidden layer. Such a structure containing cycles is referred to as a "recurrent neural network". In contrast, a neural network which does not contain cycles is referred to as a "feedforward network". The neural network model, after sufficient training, is able to predict an outcome given a test set of the same parameters used in the training. The training of a neural network is typically separated into two types: supervised learning and unsupervised learning. Unsupervised learning typically involves training data which is not labeled, tagged, or categorized while supervised learning involves labeled data. Supervised learning may be particularly useful for determining the impact of known factors on an outcome. Unsupervised learning may be particularly useful for detecting unknown factors which impact an outcome. For example, in the context of the current invention, a neural network model may accurately account for parameters which may affect a population temperature distribution, such as time of day, day of the year, or current weather conditions. In some embodiments, the artificial neural network comprises a single input layer, a single hidden layer, and a single output layer. In some embodiments, the input layer comprises 1 to 10 nodes, preferably 2 to 7 nodes, preferably 3 to 5 nodes. In some embodiments, the hidden layer comprises 1 to 25 nodes, preferably 2 to 20 nodes, preferably 5 to 15 nodes, preferably 7 to 12 nodes, preferably 10 nodes. In some embodiments, the hidden layer nodes have a sigmoid activation function. In some embodiments, the output layer node(s) have a linear activation function. In preferred embodiments, the neural network is a feedforward neural network.

Figure 2A:
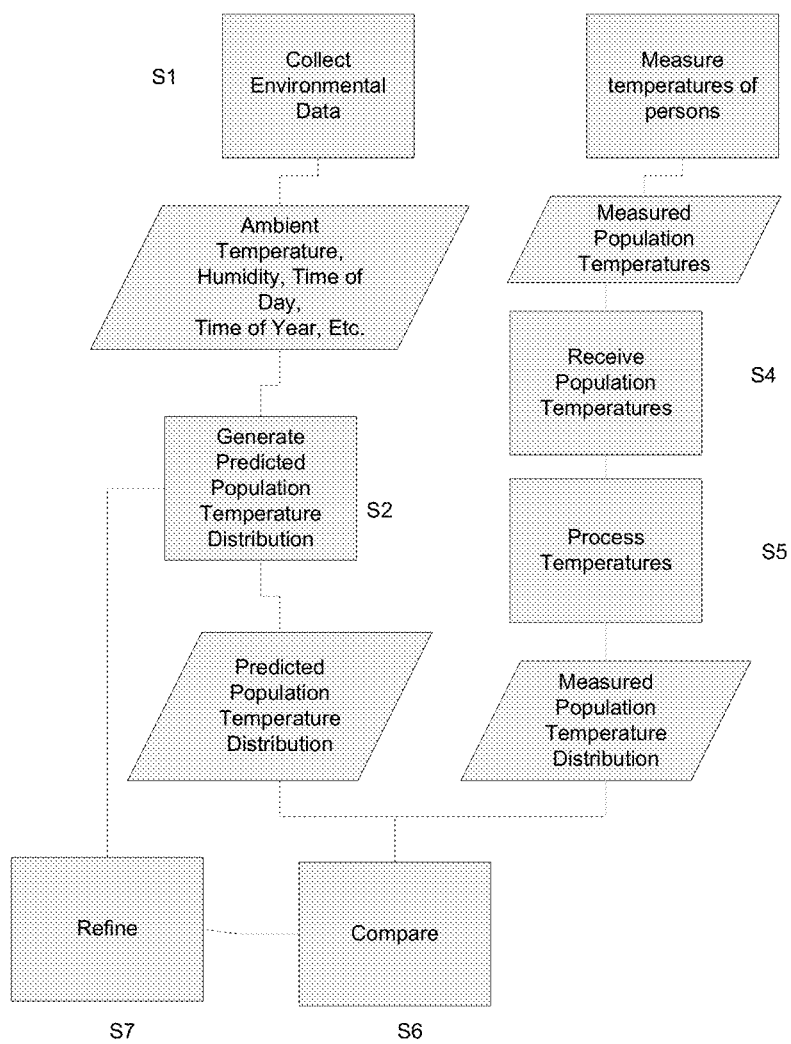
FIG. 2A is a flowchart outlining the training of an artificial neural network used in some embodiments of the fever-causing disease outbreak detection system showing steps of collecting environmental data (S1), generating predicted population temperature distribution (S2), measuring temperatures of persons (S3), receiving population temperatures (S4), processing the population temperatures to form a measured population temperature distribution (S5); comparing the predicted population temperature distribution to the measured population temperature distribution (S6), and refining the generation of the predicted population temperature distribution by the machine learning model or algorithm (S7)
Figure 2B:
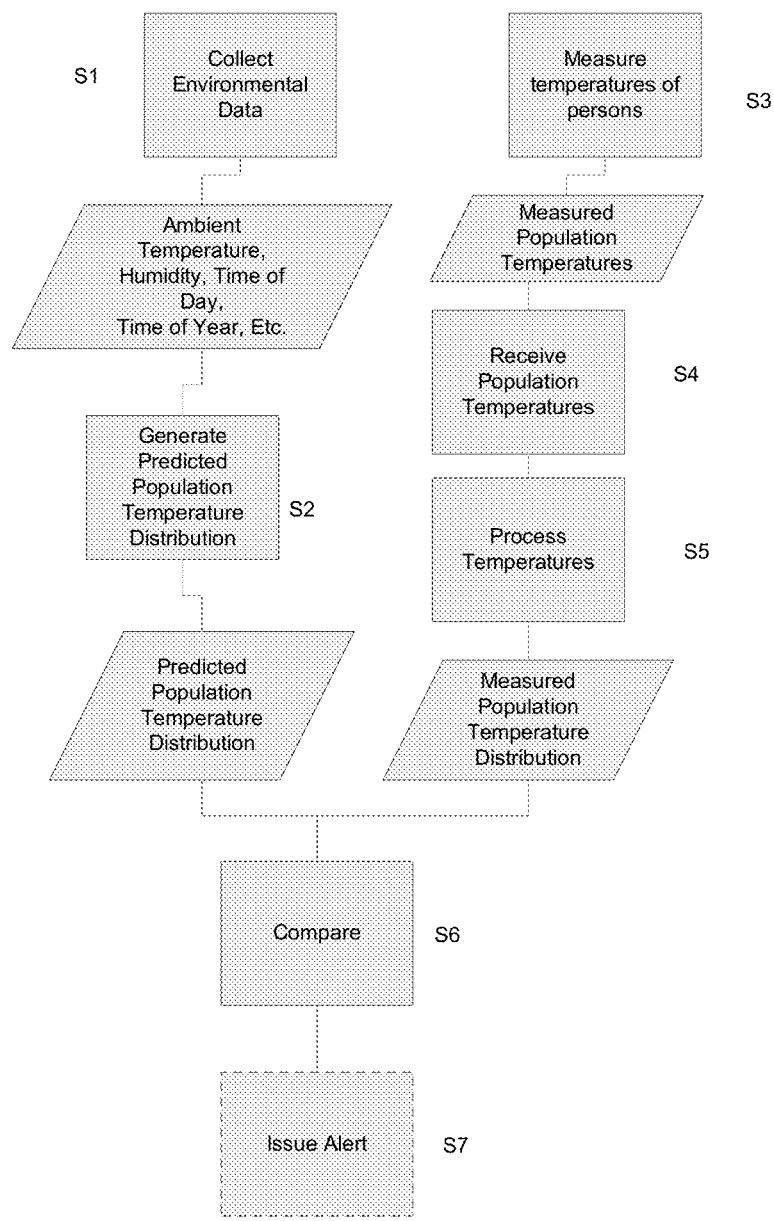
FIG. 2B is a flowchart outlining the functioning of some embodiments of the fever-causing disease outbreak detection system showing steps of collecting environmental data (S1), generating predicted population temperature distribution (S2), measuring temperatures of persons (S3), receiving population temperatures (S4), processing the population temperatures to form a measured population temperature distribution (S5); comparing the predicted population temperature distribution to the measured population temperature distribution (S6), and optionally issuing an alert (S7)
Figure 3A:
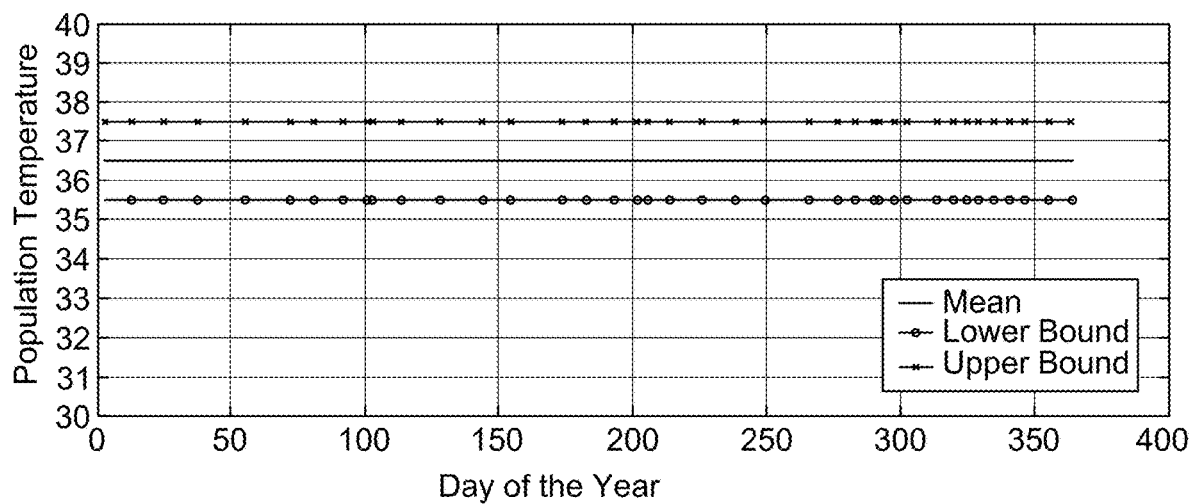
FIGS. 3A-3C are plots of temperature vs day of year produced by the machine learning model where in FIG. 3A the model does not account for seasonal variation in temperature, in FIG. 3B, the model does account for seasonal variation in temperature, and in FIG. 3C the model accounts for seasonal variation in temperature and can compare to measured data to detect an outbreak.
Figure 3B:
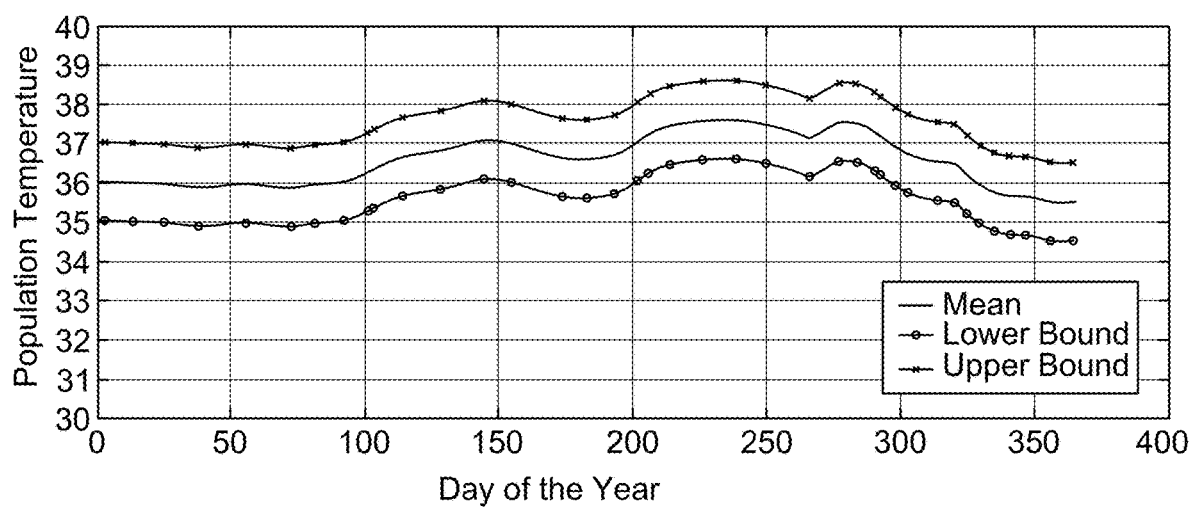
Figure 3C:
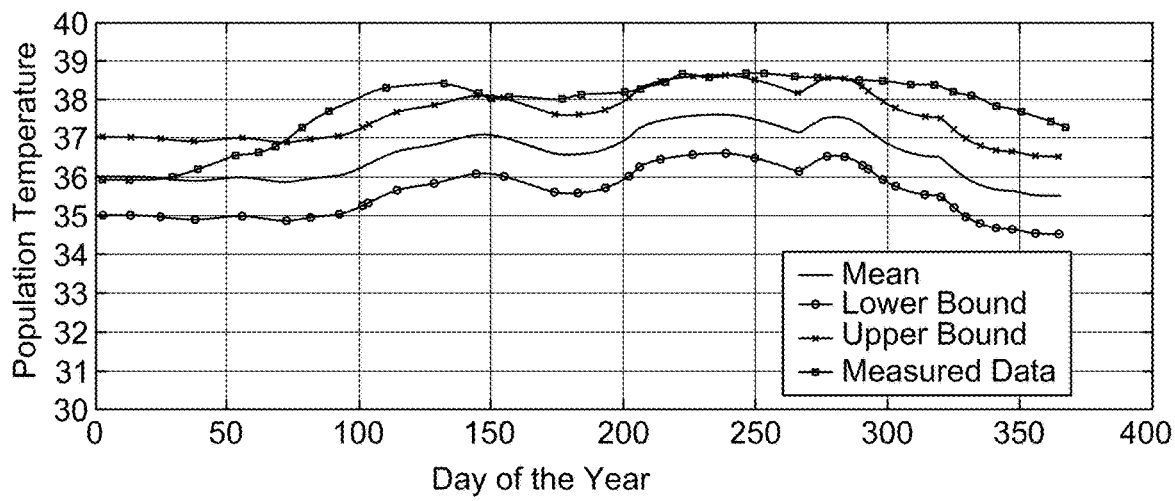

In some embodiments, the machine learning algorithm or model uses a previously measured population temperature distribution as a training dataset. In some embodiments, the previously measured population temperature distribution has a known number of individuals who had a fever at the time of measurement. In some embodiments, the previously measured population temperature distribution is devoid of individuals who had a fever at the time of the measurement. In some embodiments, the previously measured population temperature distribution has environmental data included or associated, the environmental data being as described above. Such an approach may be referred to as supervised learning. A flowchart outlining the steps of training the machine learning algorithm or model in some embodiments in which the machine learning algorithm of model uses a previously measured population temperature distribution as a training dataset is shown in FIG. 2A. Briefly, the flowchart shows the steps of collecting environmental data (S1), generating predicted population temperature distribution (S2), measuring temperatures of persons (S3), receiving population temperatures (S4), processing the population temperatures to form a measured population temperature distribution (S5); comparing the predicted population temperature distribution to the measured population temperature distribution (S6), and refining the generation of the predicted population temperature distribution by the machine learning model or algorithm (S7). The steps involved in the use of the machine learning algorithm or model as part of the system are shown in FIG. 2B, which depicts steps of collecting environmental data (S1), generating predicted population temperature distribution (S2), measuring temperatures of persons (S3), receiving population temperatures (S4), processing the population temperatures to form a measured population temperature distribution (S5); comparing the predicted population temperature distribution to the measured population temperature distribution (S6), and optionally issuing an alert (S7). In an exemplary embodiment, the machine learning algorithm or model may provide data such as a measured population temperature mean with upper and lower bounds (of, for example, +/−1° C.) as shown in FIGS. 3A-3C. In FIG. 3A, before training with the environmental data, the predicted population temperature distribution and/or mean is expected to show no seasonal variation. In FIG. 3B, after training as described above, seasonal variation in the predicted population temperature distribution may be modeled. Such modeling allows the system to detect both normal seasonal variations in measured population temperature distribution and abnormal variations which indicate a disease outbreak (see FIG. 3C).

The array of infrared detectors proves at least a portion of the measured data comprising the temperatures of persons in the measured population. In preferred embodiments, said portion comprises the temperatures of persons in the measured population. In preferred embodiments, the temperatures of persons in the measured population are measured using the array of infrared detectors. Such measured data comprising the temperatures of persons in the measured population may be provided in a variety of forms, including, but not limited to, instantaneous point thermal measures, time-averaged point thermal measures, continuous point thermal measures, and thermal images. In some embodiments, the thermal images comprise one or more persons. In general, the infrared detectors may use any suitable infrared sensor or infrared detector technology known to one of ordinary skill in the art. Examples of such sensors or detector technologies are infrared pyrometers (also called laser thermometers, non-contact thermometers, or temperature guns), bolometers and microbolometers, thermocouples, thermopiles, pyroelectric detectors, IR-sensitive film, charge-coupled device (CCD) detectors, photodiodes, photocathodes, photoresistors, and transistor-based detectors such as metal-oxide-semiconductor (MOS) detectors, complementary metal-oxide-semiconductor (CMOS) detectors, and thin-film transistor detectors. In some embodiments, the infrared detectors comprise active-pixel sensors. Active-pixel sensors are image sensors in which each pixel or sensor unit cell comprises a photodetector and one or more active transistors which act as amplifiers. In alternative embodiments, the infrared detectors comprise passive-pixel sensors. Passive-pixel sensors are image sensors in which each pixel or sensor unit cell comprises a photodetector, typically a photodiode, and a switch, but lacking an amplifier.

In some embodiments, the infrared detectors are connected to the central control unit via an internet connection. In some embodiments, the infrared detectors are selected from the group consisting of mounted thermal imaging cameras, handheld thermal imaging cameras, wearable thermal imaging cameras, and smart thermometers.

In some embodiments, the infrared detectors are mounted thermal imaging cameras. In some embodiments, the mounted thermal imaging detectors are mounted in "pinch points". Pinch points refer to places or areas which serve as checkpoints, bottlenecks, restricted thoroughfares, or other population- or traffic-limiting function. Examples of pinch points are entryways, exits, stairs, ramps, escalators, security checkpoints such as metal detectors, body scanners, or credentials checks, boarding platforms or jet ways, and ticket checkpoints. Pinch points may exits where traffic of individuals is restricted as part of entry to or exit from a population center. In some embodiments, the mounted thermal imaging cameras are stationary. In alternative embodiments, the mounted thermal imaging cameras are non-stationary. Non-stationary mounted thermal imaging cameras may be adjustable, either manually or automatically, the adjustment being a change in a vertical position (also known as height) of the camera, a horizontal position of the camera, a depth position of the camera, a vertical direction of the camera (also known as tilt), a horizontal direction of the camera (also known as pan), or a combination of these. For example, a stationary mounted thermal imaging camera may be permanently affixed to a support structure such as a wall, pillar, or ceiling that supports the thermal imaging camera such that the thermal imaging camera does not change position or direction. Such a stationary mounted thermal imaging camera would image a single portion of 3D space. In another example, a non-stationary mounted thermal imaging camera would be mounted as before except able to pan so as to image a larger portion of 3D space compared to a stationary thermal imaging camera. In another example, a non-stationary mounted thermal imaging camera may be mounted or affixed to a mobile support, such as a cart, gantry, trolley, arm, or other mobile support known to one of ordinary skill in the art, such that the position and/or direction of the camera may be adjusted. In such an example, the camera may have a fixed direction but an adjustable height so as to capture a face-on thermal image of a single person, the height of the thermal imaging camera being adjusted to match a height of the single person or feature of the single person, such as the eyes. In yet another example, a pair of stationary may be mounted at different heights so as to focus on two height ranges. In such an example, one height may be an "adult height" adjusted so as to be an appropriate height for adult individuals and the other height may be a "child height" adjusted so as to be an appropriate height for children.

In some embodiments, the infrared detectors are handheld thermal imaging cameras. In some embodiments, the handheld thermal imaging cameras are standalone thermal imaging cameras. Such standalone thermal imaging cameras may be connected to a wireless connectivity device which wirelessly connects to other components of the system. In alternative embodiments, the handheld thermal imaging cameras are combination devices, which comprise other devices or functionalities including a wireless connectivity device. Examples of such combination devices include smartphones, personal digital assistants (PDAs), tablet computers, and laptop computers. In some embodiments, the combination devices wirelessly transmit thermal images to other components of the system and wirelessly receive data or inputs from other components of the system. In such embodiments, the data or inputs received from other components of the system comprises an alert. Examples of other such data or inputs are identification information, tracking information, and instructions for a user.

In some embodiments the infrared detectors are wearable thermal imaging cameras. In some embodiments, the wearable thermal imaging cameras include a head mounted device (e.g., a helmet, a visor, eyeglasses) that the thermal imaging camera is disposed upon or attached to. In some embodiments, the head mounted device is one or a pair of eyeglasses. Such eyeglasses with thermal imaging capabilities may be commonly known as a type of "smart glasses". Smart glasses are a type of wearable computer in the form of eyeglasses which add information alongside or in addition to what a wearer sees by superimposing information into the wearer's field of vision. Such superimposition is typically achieved via an optical head-mounted display or embedded transparent head-up display (HUD) or augmented reality (AR) overlay. In the context of the present disclosure, such smart glasses would be equipped with a thermal camera which is connected wirelessly to other components of the system. An example of such a wearable thermal imaging camera is described in US20150302654A1. In some embodiments, the wearable thermal imaging camera is an augmented reality (AR) thermal camera. The AR thermal camera comprises a transparent display which typically includes lenses that are disposed in front of a user's eyes (while wearing the helmet or head mounted device) to display AR content (e.g., virtual objects). In some embodiments, the AR content comprises the temperatures or thermal images of individuals. For an example of a similar wearable AR infrared detector see U.S. Pat. No. 9,536,355 B1. Such smart glasses may be advantageous for use in the system of the present disclosure by allowing mobile, human-directed collection of measured data comprising the temperatures of individuals. A healthcare worker, police officer, or other user may use such a wearable infrared detector to measure the temperatures of individuals in a measured population. In some embodiments, the wearable thermal imaging camera wirelessly transmits thermal images to other components of the system and wirelessly receives data or inputs from other components of the system as described above.

In some embodiments, the infrared detectors are smart thermometers. Smart thermometers are medical thermometers which have the capability of electronically transmitting measured data comprising the temperature of an individual to a computer or similar device. In some embodiments, the smart thermometers are equipped with wireless transmitters which wirelessly connect to other components of the system. In alternative embodiments, the smart thermometers are connected to wireless transmitters which wirelessly connect to other components of the system.

In some embodiments, the measured data comprising the temperatures of persons in the measured population is in the form of thermal images comprising one or more persons. In such embodiments, the thermal images are processed so as to obtain the temperatures of persons in the image. In some embodiments, the measured data comprising the temperatures of one or more persons in the measured population further comprises visual images comprising one or more persons. In some embodiments, the measured data comprising the temperatures of persons in the measured population comprises thermal and visual composite or fusion images. In some embodiments, the visual images are collected via one or more visual cameras. In some embodiments, the fever-causing disease outbreak detection system further comprises one or more visual cameras. In some embodiments, the visual cameras are located in substantially the same area as the infrared detectors. In some embodiments, the visual cameras are oriented so as to image substantially the same area as the infrared detectors.

In some embodiments, the thermal and/or visual images are processed by the system. In such embodiments, the fever-causing disease outbreak detection system further comprises an image processor for processing the thermal and/or visual images so as to obtain the temperatures of persons in the measured population. In alternative embodiments, the thermal and/or visual images are processed by an external image processor. The external image processor may be any image processor that is not part of the central control unit. In some embodiments, the external image processor is connected to the central control unit via a wired or wireless internet connection. In some embodiments, the thermal images are be transmitted to the external image processor by the array of infrared detectors. In alternative embodiments, the thermal and/or images are transmitted to the external image processor by the central control unit. In embodiments where the thermal and/or images are processed by the external image processor, the temperatures of persons in the measured population are received by the central control unit.

Thermal and visual images, still or video, provide a volume of temperature information for thermal and visual analysis and processing. In the case of thermal images, the data may be represented as a matrix of temperatures in which each element corresponds to a pixel in the thermal image. These pixels, in turn can be used to measure the temperature of individuals. In visual images, the data may be represented as, for example, a matrix of brightness values in which each element corresponds to a monochromatic brightness value or a single-channel brightness value corresponding to one of the color channels of the image. Image processing techniques may be applied to the temperature or brightness matrices as with any other matrix. The thermal images may be processed in a manner or using a method known to one of ordinary skill in the art. Similarly, the visual images may be processed in a manner or using a method known to one of ordinary skill in the art. Examples of such manners or methods which may be used in the thermal or visual image processing include image filtering such as median filtering, wiener filtering, matched filtering, least mean squares filtering, and Kalman filtering; image enhancement techniques such as contrast manipulation, gray level manipulation, edge enhancement, noise reduction, deconvolution, despeckling, and pseudocoloring; image segmentation techniques such as classification-based segmentation, edge-based segmentation, threshold-based segmentation, and region-based segmentation; feature extraction; thresholding; frame averaging; and object classification. Such techniques are useful in the automated detection and measurement of the temperatures of individual persons depicted in the thermal and/or visual images. In some embodiments, the processing involves the merging or fusion of one or more visual images with one or more thermal images. The result of said merging or fusion is commonly referred to as a "composite" image. The merging or fusion may be performed by any method or technique known to one of ordinary skill in the art. Examples of such methods or techniques are multi-scale transform methods such as pyramid transforms, wavelet transforms, contourlet transforms, edge-preserving filters, framelet transforms, shearlet transforms, tetrolet transforms, top-hat transforms, discrete cosine transforms, directionlet transforms, empirical mode decompositions, internal generative mechanisms, and multi-resolution singular value decompositions. Further examples of such methods or techniques are sparse representation methods which involve dictionary construction which may be accomplished by techniques or methods such as fixed-basis or learning-basis methods, coefficient-obtaining which may be accomplished by techniques or methods such as orthogonal matching pursuit, joint sparce representation models, approximate sparce representation models, and convolutional sparce representation, and fusion rules such as the Max-$L_1$ rule and the weighted average rule. Further examples of such methods or techniques are neural network and deep learning methods such as pulse-coupled neural networks (PCNNs), and convolutional neural networks (CNNs). Further examples of such methods or techniques are subspace methods such as principal component analysis (PCA), independent component analysis (ICA), and non-negative matrix factorization. Further examples of such methods or techniques are saliency methods such as weight calculation and salient object extraction. Further examples of such methods and techniques are image registration methods and hybrid methods. [Ma, J., Ma, Y., & Li, C., "Infrared and visible image fusion methods and applications: A survey", Information Fusion, 2019, 45, 153-178, incorporated herein by reference]

In some embodiments, the processing includes identification and discrimination of an individual from the background or other objects. In some embodiments, such identification and discrimination involves feature detection. In some embodiments, the feature detection is face detection. The face detection may be performed by any suitable method for face detection from thermal images and/or visual images known to one of ordinary skill in the art. An example of such a method is discussed in Markus, et. al. [N. Markus, M. Frljak, I. S. Pandzic, J. Ahlberg, and R. Forchheimer, "A method for object detection based on pixel intensity comparisons", arXiv:1305.4537 [cs.CV], May 2013, incorporated herein by reference]. In alternative embodiments, the feature detection is body detection. The body detection may be performed by any suitable method for body detection from thermal images and/or visual images known to one of ordinary skill in the art. Examples of such methods are discussed in Dollar, et. al. [P. Dollar, C. Wojek, B. Schiele and P. Perona, "Pedestrian Detection: An Evaluation of the State of the Art", IEEE Transactions on Pattern Analysis and Machine Intelligence, Volume 34, Issue 4, pp. 743-761, April 2012, incorporated herein by reference]. Body detection may be advantageous in situations in which the thermal and/or visual images do not show an individual's face. Such situations may arise if the individual is wearing a face covering such as a face mask or veil, or is wholly or partially covering his/her face in any other way such as part of the act of sneezing, or is turning the face in a direction away from the thermal and/or visual imaging device(s).

In some embodiments, the processing includes the definition of a measurement site. The measurement site may be formed by an external surface of the individual's skin from which the individual's body temperature may be measured or calculated. Examples of such measurements sites include the face, forehead, temple, ears (such as the outer or inner ear), eyes, nose, lips, neck, wrist, ankle, hand, foot, chin, open mouth, and/or other like skin surfaces. In some embodiments, the measurement site is automatically detected. In some embodiments, the measurement site is detected by feature detection as described above. In preferred embodiments, the measurement site includes the eyes. The choice of the eyes may be advantageous for accuracy of body temperature determination or for allowing body temperature determination while the individual is wearing a face covering such as a face mask or veil.

The processing of thermal and/or visual images may be advantageous for accurate measurement of temperatures of individual persons and reduce undesirable effects or data from being included in the measured data comprising the temperatures of persons in the measured population used by the system. For example, the inclusion of measured temperatures of objects which are depicted in a thermal and/or visual image but which are not persons may cause false positives or false negatives in the issued alerts. Inanimate objects, for obvious reasons, cannot exhibit fevers caused by diseases and should not be included in the data. Additionally, animals may exhibit different normal body temperatures which may be within a fever temperature range for humans. Dogs, for example, typically exhibit a normal body temperature of 101 to 102.5° F. (38.3 to 39.2° C.), which would be classified as a fever temperature for a human. It would be advantageous to exclude the temperatures of such animals so the animal's normal temperature is not mistakenly classified as a fever-having human temperature.

In some embodiments, the system is capable of identifying and tracking individuals in the measured population temperature distribution likely exhibiting a fever. In some embodiments, the identifying and tracking of individuals may be accomplished by using thermal images or thermal videos, optionally in combination with visual images or visual video. This identifying and tracking of individuals may be advantageous for accurate population-level temperature measurements. One problem which may arise is that an individual must be counted only once in the measured population despite the fact that said individual could possibly be counted many times such as by being present in multiple thermal images from a single infrared detector, being present for more than one frame in a thermal video from a single infrared detector, or being captured by more than one infrared detector. If a single individual, for example, walks from an area covered by one infrared detector to another, it would be advantageous to have the system recognize that said individual represents one measured temperature in the measured population temperature distribution and not multiple separate individuals. Another example of a situation in which identifying and tracking individuals may be advantageous is if a single fever-exhibiting individual is preset in an area for an extended period of time such that they are present in multiple temporally-spaced sequential measurements. If such an individual were counted as a unique individual in the measured temperature population distribution, a false positive alert could be issued as the fever of that individual would be counted toward a total number of fevers multiple times. This identifying and tracking of individuals may also be advantageous for interception of, isolation of, or providing medical attention to a fever-exhibiting individual even if said individual is moving through an area in which the array of infrared detectors is distributed.

In some embodiments, the array of infrared detectors is distributed across and measures the temperatures of persons within population centers selected from the group consisting of transit facilities such as airports, train stations, metro stations, and bus stations or depots; healthcare facilities such as hospitals and clinics; commercial centers such as shopping malls, markets, food courts or food halls, and amusement parks; public parks; residential facilities such as apartment buildings, condominium buildings, and neighborhoods; and work facilities such as office buildings and factories. Such population centers may be chosen due to the large number of people that spend time in or pass through them. In some embodiments, the array of infrared detectors at each population center may have a dedicated central control unit. In some embodiments, arrays of infrared detectors placed in multiple population centers within a geographic area, such as a city, state, province, region, or country may be connected to a single central control unit.

In some embodiments, the fever-causing disease outbreak detection system further comprises non-infrared-detector-containing thermometers. Examples of such thermometers are liquid-filled thermometers, mercury thermometers, phase-change (also called dot matrix) thermometers, and liquid crystal thermometers. Such non-infrared-detector-containing thermometers may be smart thermometers as described above. In such embodiments, the smart non-infrared-detector-containing thermometers may transmit measured data comprising the temperatures of individuals to the central control unit. Alternatively, measured data comprising the temperatures of individuals may be transmitted to the system by the use of an app as described below.

Figure 4:
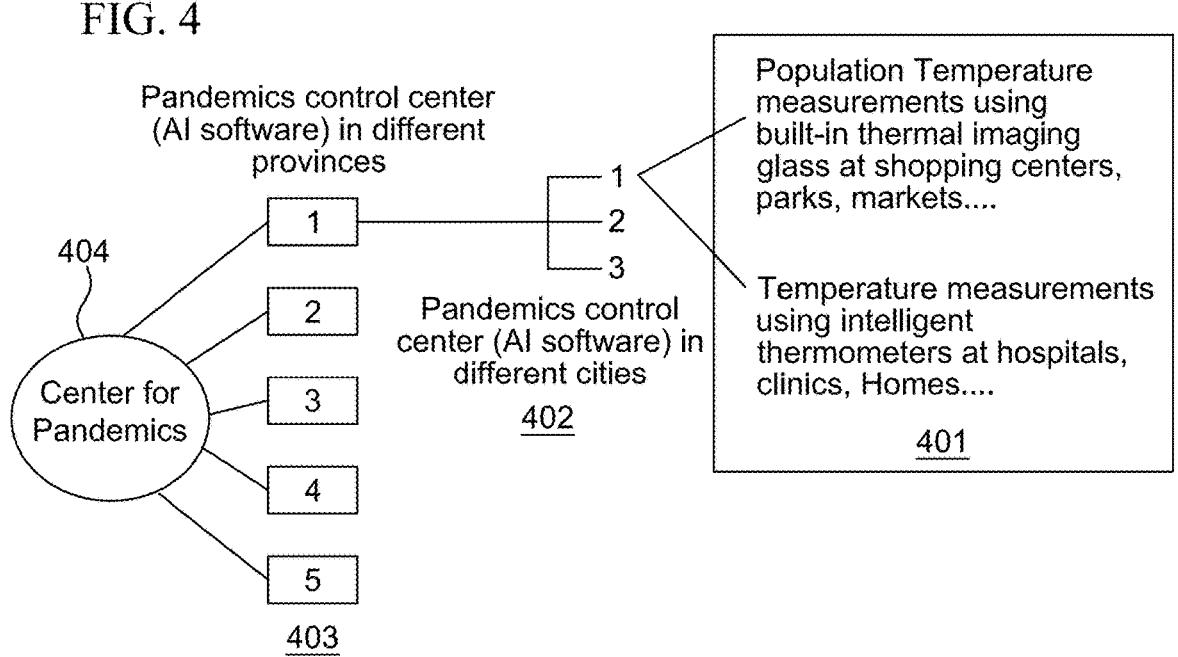
FIG. 4 is a diagram depicting a hierarchical fever-causing disease outbreak detection system distributed over a geographical area.

In some embodiments, the fever-causing disease outbreak detection system has a hierarchical structure characterized by two or more primary central control units, each connected to one or more arrays of infrared detectors, the primary central control units being connected to one or more secondary central control units. In some embodiments, the secondary central control units are connected to a tertiary central control unit. A depiction of such a hierarchical structure is shown in FIG. 4, which depicts the arrays of infrared detectors (401), primary control centers (402), secondary control centers (403), and tertiary control center (404).

Method of Detecting a Fever-Causing Disease Outbreak

The present disclosure also relates to a method of detecting a fever-causing disease outbreak. The method comprises measuring temperatures of persons in a measured population using an array of infrared detectors, receiving via an internet connection the temperatures at a central control unit, processing the temperatures to form a measured population temperature distribution, generating a predicted population temperature distribution, comparing the measured population temperature distribution to the predicted population temperature distribution to determine an outbreak condition, and optionally issuing an alert if the outbreak condition meets an alert criterion.

In some embodiments, the measuring is performed with one or more infrared detectors selected from the group consisting of mounted thermal imaging cameras, handheld thermal imaging cameras, wearable thermal imaging cameras, and smart thermometers as described above.

In some embodiments, the measuring comprises obtaining one or more thermal images and extracting from the thermal images the temperatures of persons depicted in the images. In some embodiments, the extracting is performed by one or more image processing manners or methods as described above. The image processing may be performed by an image processor that is part of the system described above or by an external image processor.

In general, the processing of the temperatures to form a measured population temperature distribution may use a technique or method known to one of ordinary skill in the art. Examples of such techniques or methods are sorting, rejection of outliers, binning, and merging.

In some embodiments, the generating is performed using a machine learning algorithm or model as described above. In some embodiments, the machine learning algorithm or models is an artificial neural network as described above.

In some embodiments, the method further comprises collecting at least one environmental data selected from the group consisting of ambient temperature, ambient temperature history, room temperature, room temperature history, local atmospheric temperature, local atmospheric temperature history, humidity, humidity history, time of day, time of year, secondary location temperature, and secondary location temperature history as described above. Such environmental data may be used in the generating as described above. Such environmental data may be used by the machine learning algorithm or model and/or artificial neural network as described above.

In some embodiments, the comparing is performed using statistical analytical techniques. In general, any statistical analytical technique known to one of ordinary skill in the art may be used. Of particular importance are statistical analytical techniques that compare two populations or distributions, such as comparisons of means, modes, medians, standard deviations, variances, skewness, kurtosis, or other descriptive statistic. In some embodiments, the comparing compares the mean of the predicted population temperature distribution to the mean of the measured population temperature distribution. In some embodiments, the comparing compares the median of the of the predicted population temperature distribution to the median of the measured population temperature distribution. In some embodiments, the comparing compares the standard deviation of the of the predicted population temperature distribution to the standard deviation of the measured population temperature distribution. In some embodiments, the comparing involves two or more descriptive statistics, such as median and mean, median and standard deviation, or mean and standard deviation. In some embodiments, the comparing compares the skewness of the of the predicted population temperature distribution to the skewness of the measured population temperature distribution. In general, the skewness may be any skewness measure known to one of ordinary skill in the art. Examples of skewness measures include, but are not limited to non-parametric skewness, L-moments, Groenveld & Meeden's coefficient, distance skewness, medcouple, Bowley's skewness, Pearson's first skewness coefficient, and Pearson's second skewness coefficient. In some embodiments, the comparing compares the kurtosis of the of the predicted population temperature distribution to the kurtosis of the measured population temperature distribution. In some embodiments, the comparing involves the use of statistical algorithms. In general, any statistical algorithm known to one of ordinary skill in the art may be used. Examples of such statistical algorithms include the Early Aberration Reporting System (EARS), rising activity multilevel mixed effects indicator emphasis (RAMMIE) method, and the quasi-Poisson regression based exceedance (also known as Farrington Flexible) method. Such statistical algorithms are discussed in Noufaily, et. al. [Angela Noufaily, Roger A Morbey, Felipe J Colón-González, Alex J Elliot, Gillian E Smith, Iain R Lake, Noel McCarthy, Comparison of statistical algorithms for daily syndromic surveillance aberration detection, Bioinformatics, Volume 35, Issue 17, 1 Sep. 2019, Pages 3110-3118, incorporated herein by reference]. In some embodiments, the comparing results in a single outbreak parameter. In some embodiments, the alert criterion comprises a threshold value of the single outbreak parameter. In some embodiments, the alert criterion is adjustable. In some embodiments, the alert criterion may be adjusted manually. In alternative embodiments, the alert criterion may be adjusted automatically. In such embodiments, the alert criterion may be adjusted by a machine learning algorithm or model. In some embodiments, the alert criterion comprises an elevated measured population temperature distribution mean greater than a predicted population temperature distribution mean by at least 1.0° C.

In some embodiments, the comparing is performed by a machine learning algorithm or model as described above. In some embodiments, the machine learning algorithm or models is an artificial neural network as described above. In some embodiments, the machine learning algorithm of model uses statistical analytical techniques as described above.

In some embodiments, the comparing involves predicted and measured population temperature distributions which contain data aggregated over the course of a time period. In general, any time period may be used. Examples of time periods of particular interest to the current invention include, but are not limited to 1 minute, 10 minutes, 15 minutes, 30 minutes, 45 minutes, one hour, 4 hours, 6 hours, 8 hours, 12 hours, 24 hours, two days, three days, five days, one week, two weeks, three weeks, and one month. In some embodiments, the comparing detects the presence of a statistically higher number of individuals with elevated body temperatures in the measured population temperature distribution compared to the predicted population temperature distribution. In some embodiments, the statistically higher number of individuals with elevated body temperatures occurs over a time period as described above. The alert criterion may be defined by the details of the comparing.

In some embodiments, the method further comprises identifying and tracking individuals in the measured population temperature distribution likely exhibiting a fever as described above.

In some embodiments, the fever-causing disease outbreak detection system described above achieves certain functions via the use of a mobile application (often referred to as an App, or mobile App, or smartphone App). An App may be software that can be installed in various platforms, such as a laptop computer, tablet computer, smartphone, or other mobile device. In some embodiments, certain portions of the method for detecting the outbreak of a fever-causing disease described above may be achieved via the use of an App. Examples of the certain functions achieved via the use of the App for the system, the method, or both, include, but are not limited to, the transmitting or receiving of measured data, the transmitting or receiving of environmental data, the issuing of an alert, the transmitting of thermal and/or visual images to be processed by an external image processor, and the receiving of data from an external image processor. For example, the App may include a function allowing a user to input temperatures of individuals collected without the use of the infrared detectors that are part of the system as described above. In such cases, the temperatures of individuals may be manually collected, for example by trained healthcare professionals at medical facilities, and transmitted to the central control unit by the App or other piece of software. In another example, the App may be used to collect or transmit to the central control unit environmental data or location data. Such a function may be advantageous in embodiments of the system which use handheld and/or wearable thermal imaging cameras.

A depiction of the steps of an exemplary embodiment of the method are shown in FIG. 2B, which depicts steps of collecting environmental data (S1), generating predicted population temperature distribution (S2), measuring temperatures of persons (S3), receiving population temperatures (S4), processing the population temperatures to form a measured population temperature distribution (S5); comparing the predicted population temperature distribution to the measured population temperature distribution (S6), and optionally issuing an alert (S7).

Non-Transitory Processor Readable Medium

The present disclosure is also related to a non-transitory processor readable medium having processor instructions that are executable to cause a processor to generate a predicted population temperature distribution using a machine learning algorithm or model, generate a measured population temperature distribution using a plurality of measured temperatures of persons, compare the measured population temperature distribution to the predicted population temperature distribution, and issue an alert-generating output if the comparing meets an alert criterion.

Figure 5:
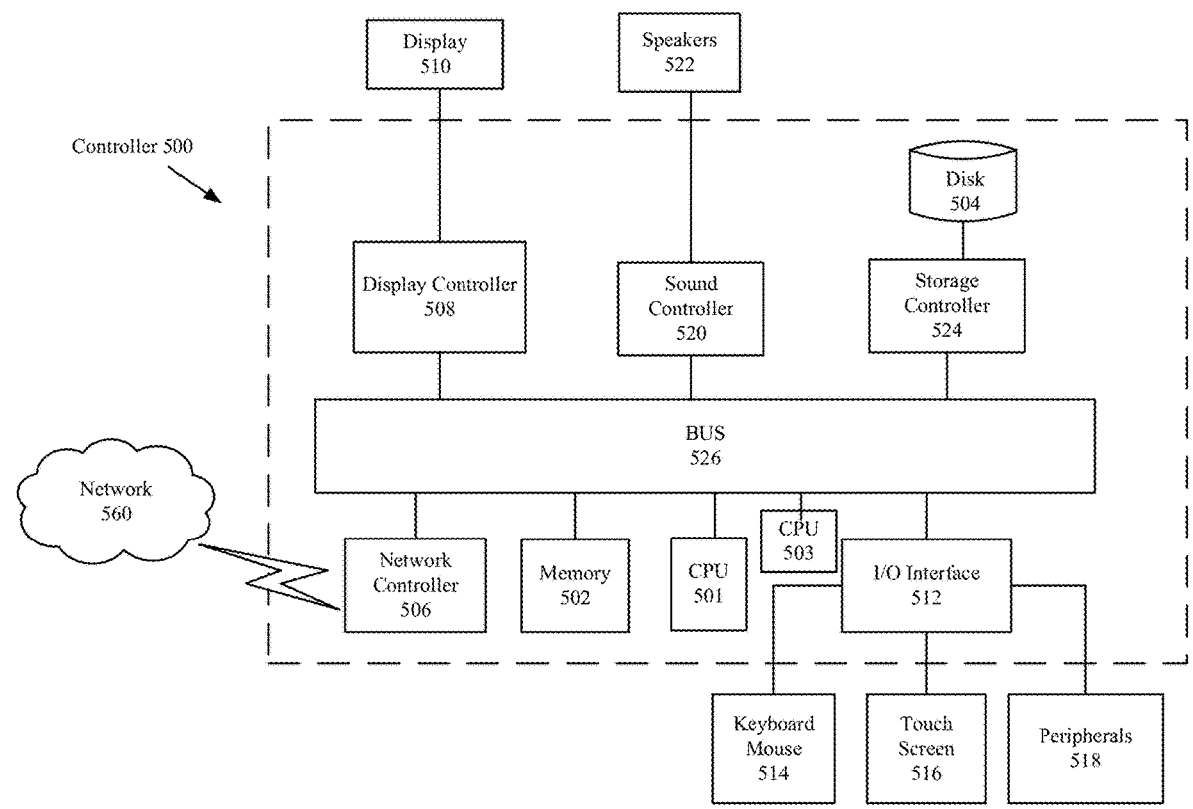
FIG. 5 is an illustration of a non-limiting example of details of computing hardware used in the computing system, according to certain embodiments.

Next, a hardware description of the fever-causing disease outbreak detection system or component thereof, such as the central control unit, measurement processing unit, prediction generating unit, or image processor according to exemplary embodiments is described with reference to FIG. 5. In FIG. 5, the system includes a CPU 500 which performs the processes described above. The process data and instructions may be stored in memory 502. These processes and instructions may also be stored on a storage medium disk 504 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the system communicates, such as a server or computer.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 501, 503 and an operating system such as Microsoft Windows 7, Microsoft Windows 10, UNIX, Solaris, LINUX, Apple MAC-OS and other systems known to those skilled in the art.

The hardware elements in order to achieve the computing device may be realized by various circuitry elements, known to those skilled in the art. For example, CPU 501 or CPU 503 may be a Xenon or Core processor from Intel of America or an Opteron processor from AMD of America, or may be other processor types that would be recognized by one of ordinary skill in the art. Alternatively, the CPU 501, 503 may be implemented on an FPGA, ASIC, PLD or using discrete logic circuits, as one of ordinary skill in the art would recognize. Further, CPU 501, 503 may be implemented as multiple processors cooperatively working in parallel to perform the instructions of the inventive processes described above.

The computing device in FIG. 5 also includes a network controller 506, such as an Intel Ethernet PRO network interface card from Intel Corporation of America, for interfacing with network 560. As can be appreciated, the network 560 can be a public network, such as the Internet, or a private network such as an LAN or WAN network, or any combination thereof and can also include PSTN or ISDN sub-networks. The network 560 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 508, such as a NVIDIA GeForce GTX or Quadro graphics adaptor from NVIDIA Corporation of America for interfacing with display 510, such as a Hewlett Packard HPL2445w LCD monitor. A general purpose I/O interface 512 interfaces with a keyboard and/or mouse 514 as well as a touch screen panel 516 on or separate from display 510. General purpose I/O interface also connects to a variety of peripherals 518 including printers and scanners, such as an OfficeJet or DeskJet from Hewlett Packard.

A sound controller 520 is also provided in the computing device such as Sound Blaster X-Fi Titanium from Creative, to interface with speakers/microphone 522 thereby providing sounds and/or music.

The general purpose storage controller 524 connects the storage medium disk 504 with communication bus 526, which may be an ISA, EISA, VESA, PCI, or similar, for interconnecting all of the components of the computing device. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 6.

Figure 6:
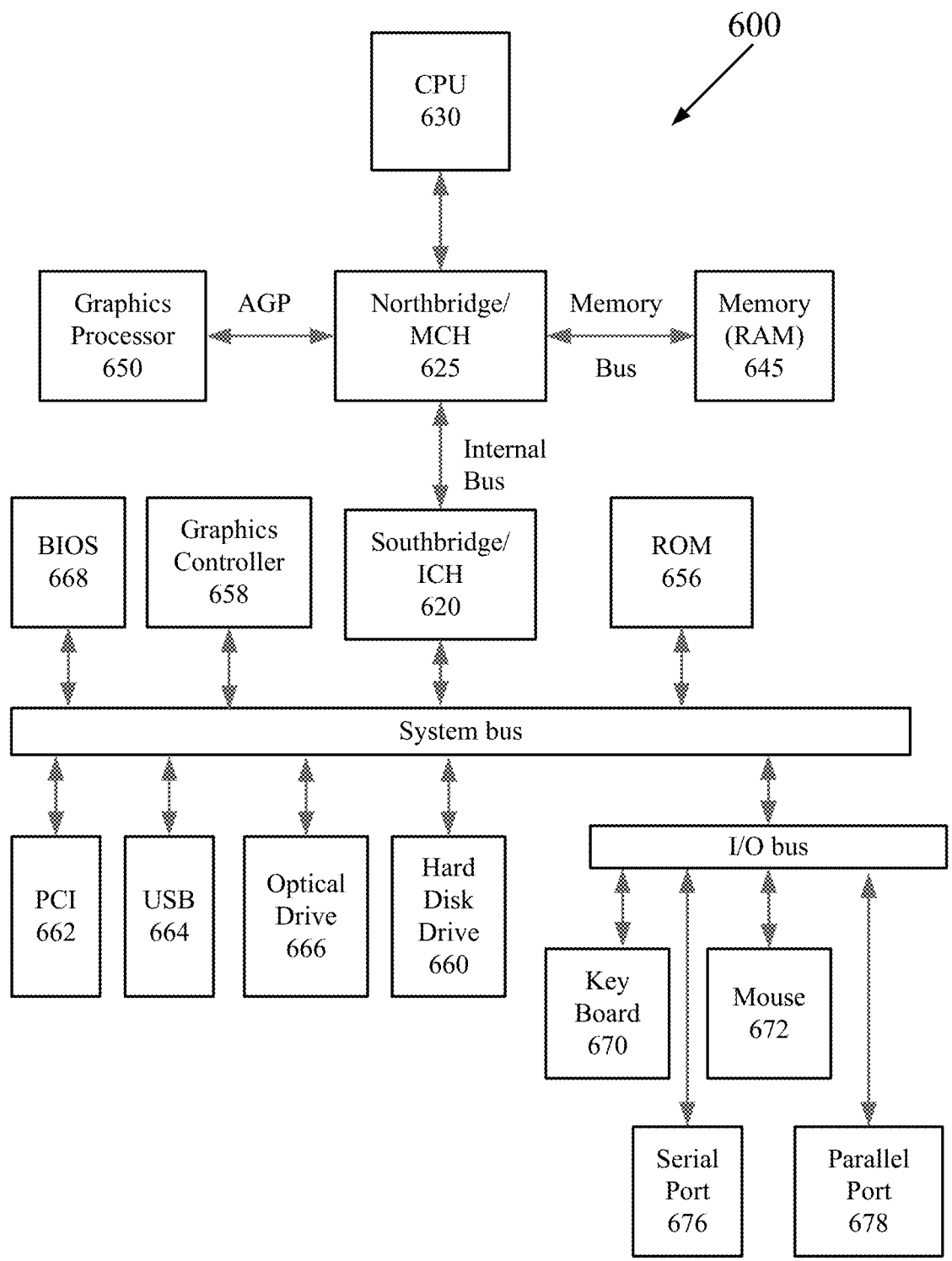
FIG. 6 is an exemplary schematic diagram of a data processing system used within the computing system, according to certain embodiments.

FIG. 6 shows a schematic diagram of a data processing system, according to certain embodiments, for performing the functions of the exemplary embodiments. The data processing system is an example of a computer in which code or instructions implementing the processes of the illustrative embodiments may be located.

In FIG. 6, data processing system 600 employs a hub architecture including a north bridge and memory controller hub (NB/MCH) 625 and a south bridge and input/output (I/O) controller hub (SB/ICH) 620. The central processing unit (CPU) 630 is connected to NB/MCH 625. The NB/MCH 625 also connects to the memory 645 via a memory bus, and connects to the graphics processor 650 via an accelerated graphics port (AGP). The NB/MCH 625 also connects to the SB/ICH 620 via an internal bus (e.g., a unified media interface or a direct media interface). The CPU Processing unit 630 may contain one or more processors and even may be implemented using one or more heterogeneous processor systems.

Figure 7:
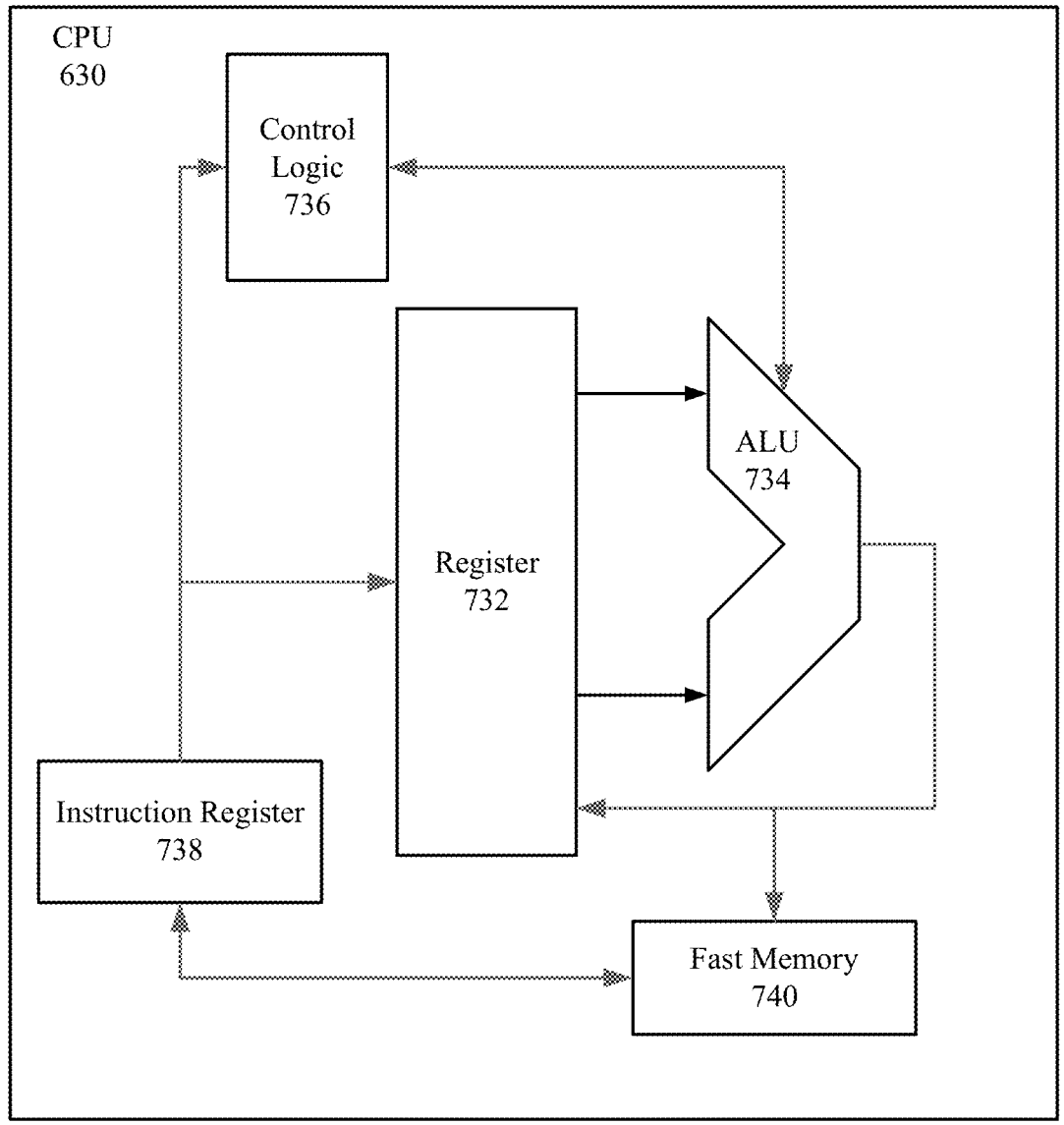
FIG. 7 is an exemplary schematic diagram of a processor used with the computing system, according to certain embodiments.

For example, FIG. 7 shows one implementation of CPU 630. In one implementation, the instruction register 738 retrieves instructions from the fast memory 740. At least part of these instructions are fetched from the instruction register 738 by the control logic 736 and interpreted according to the instruction set architecture of the CPU 630. Part of the instructions can also be directed to the register 732. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 734 that loads values from the register 732 and performs logical and mathematical operations on the loaded values according to the instructions. The results from these operations can be feedback into the register and/or stored in the fast memory 740. According to certain implementations, the instruction set architecture of the CPU 630 can use a reduced instruction set architecture, a complex instruction set architecture, a vector processor architecture, a very large instruction word architecture. Furthermore, the CPU 630 can be based on the Von Neuman model or the Harvard model. The CPU 630 can be a digital signal processor, an FPGA, an ASIC, a PLA, a PLD, or a CPLD. Further, the CPU 630 can be an ×86 processor by Intel or by AMD; an ARM processor, a Power architecture processor by, e.g., IBM; a SPARC architecture processor by Sun Microsystems or by Oracle; or other known CPU architecture.

Referring again to FIG. 6, the data processing system 600 can include that the SB/ICH 620 is coupled through a system bus to an I/O Bus, a read only memory (ROM) 656, universal serial bus (USB) port 664, a flash binary input/output system (BIOS) 668, and a graphics controller 658. PCI/PCIe devices can also be coupled to SB/ICH 688 through a PCI bus 662.

The PCI devices may include, for example, Ethernet adapters, add-in cards, and PC cards for notebook computers. The Hard disk drive 660 and CD-ROM 666 can use, for example, an integrated drive electronics (IDE) or serial advanced technology attachment (SATA) interface. In one implementation the I/O bus can include a super I/O (SIO) device.

Further, the hard disk drive (HDD) 660 and optical drive 666 can also be coupled to the SB/ICH 620 through a system bus. In one implementation, a keyboard 670, a mouse 672, a parallel port 678, and a serial port 676 can be connected to the system bus through the I/O bus. Other peripherals and devices that can be connected to the SB/ICH 620 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 8:
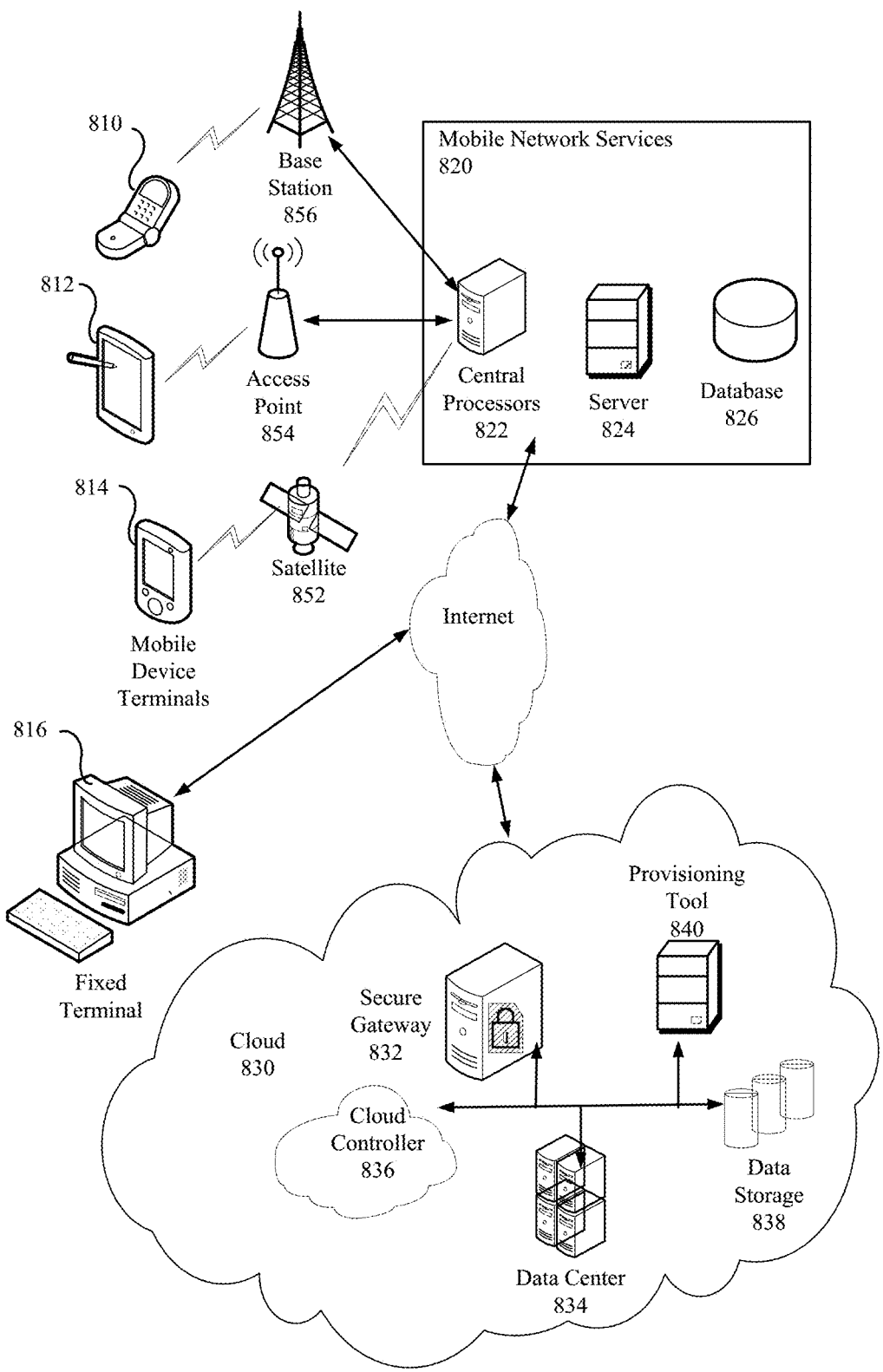
FIG. 8 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 8, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

In some embodiments, the predicted population temperature distribution is generated with at least one additional input data selected from the group consisting of ambient temperature, ambient temperature history, room temperature, room temperature history, local atmospheric temperature, local atmospheric temperature history, humidity, humidity history, time of day, time of year, secondary location temperature, and secondary location temperature history as described above.

The examples below are intended to further illustrate the fever-causing disease outbreak detection system and protocols for the method of detecting the outbreak of a fever-causing disease and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

One embodiment of the current invention is an early warning system based on the utilization of glasses with built-in thermal imaging capabilities and/or intelligent thermometers to measure and gather data on the mass population temperature. Accordingly, the smart glasses are employed at shopping centers, markets, parks, train stations, airports, etc., and intelligent thermometer are used at hospitals, clinics and homes to monitor, record and report individual measured temperatures in a population. The real time temperature data is then transferred to an app which can be used to alert the authorities of the spread of epidemic/pandemics (Corona, influenza). Mass population temperatures are measured via internet connected glasses and thermometers consciously and are transmitted to the center for pandemic control for the city/province/country. At these centers with the help of a specialized app, areas of pandemic are identified.

Training the Neural Network Temperature Model

Figure 9:
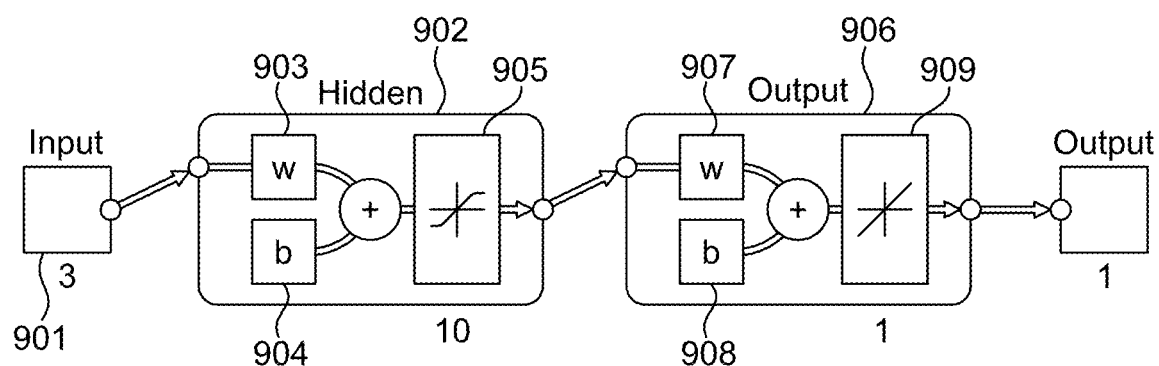
FIG. 9 is a diagram of an example of a neural network model.

The neural network temperature model for the population is a model that predicts population temperature based on weather and relevant seasonality conditions. It uses sensory information such as ambient temperature, humidity, time of the day, and day of the year. The temperature data collected from the thermal imaging glasses and/or thermometers are used to train the neural network (FIG. 2A). Once training criteria is met (suitable sample data, convergence of the training, etc.) the temperature model it can be used to detect measurable changes in temperature of the population (FIG. 2B). Before training, the neural network temperature model does not account for seasonal variation in temperature distribution (FIG. 3A). After training, however, such variation may be accurately modeled (FIG. 3B), allowing for accurate detection of abnormal temperature distributions indicating disease outbreaks (FIG. 3C). An example of a neural network model is depicted in FIG. 9, showing the input layer (901) made up of 3 nodes, the hidden layer (902) made up of 10 nodes, each having a weighted connection from one or more inputs (903), a bias (904), and a sigmoid activation function (905), and the output layer (906) made up of one node having a weighted connection from each node of the hidden layer (907), a bias (908), and a linear activation function (909).

Features of the System:

IoT infra-red enabled wearable glasses are used to record temperature measurements in social hubs also, intelligent thermometers are used to record temperature at hospitals, clinics and homes. This allows for fast capturing and recording of temperature data. The data is sent to the cloud in real time. This allows real time processing. Processing includes removal of outlier data, seasonal changes in temperature, relative comparisons between cities, airport hubs and malls. It also includes absolute changes in temperature.

Processing also includes parsing data from multiple sensors and geo-labeling such data.

The invention claimed is:

1. A thermal imaging system for disease outbreak detection, comprising:
   a central control unit comprising:
      a wireless connection device,
      a measurement processing unit,
      a prediction generating unit, and
      an alert output device; and
   a restricted thoroughfare that is an entry or exit to a population center and that restricts traffic of individuals of a measured population;
   an array of infrared detectors wirelessly connected to the central control unit,
   wherein the array of infrared detectors measures temperatures of the individuals in the measured population, wherein the array of infrared detectors is mounted stationary at the restricted thoroughfare to capture thermal images of a plurality of individuals of the measured population;
   at least one non-stationary thermal image camera mounted to a mobile support and wirelessly connected to the central control unit, wherein the non-stationary thermal image camera is configured to pan the restricted thoroughfare,
   wherein the at least one non-stationary thermal image camera is height adjustable to capture a face-on thermal image of a single individual of the measured population and configured such that the height of the at least one thermal imaging camera is adjusted to match a height of the single individual of the measured population at eye level when capturing a thermal image of the single individual of the measured population;
   an environmental observation system including a thermal imaging device to measure a temperature of the environment at the restricted thoroughfare and wirelessly connected to the central control unit; and
   wherein the central control unit:
      receives measured data comprising the temperatures of the plurality of individuals in the measured population via the wireless connection device,
      processes the temperatures using the measurement processing unit to form a measured population temperature distribution,
      generates a predicted population temperature distribution based on the temperature of the environment at the restricted thoroughfare with an artificial neural network using the prediction generating unit,
      compares the measured population temperature distribution to the predicted population temperature distribution to determine an outbreak condition,
      identifies any individuals having a fever, and
      issues an alert when the outbreak condition meets an alert criterion using the alert output device.

2. The thermal imaging system for disease outbreak detection of claim 1, wherein the central control unit further comprises an environmental data collection unit which receives environmental data including the temperature of the environment at the restricted thoroughfare from the environmental observation system.

3. The thermal imaging system for disease outbreak detection of claim 1, wherein the infrared detectors are connected to the central control unit via an internet connection.

4. The thermal imaging system for disease outbreak detection of claim 1, further comprising an image processor which processes the thermal images so as to obtain the temperatures of the individuals in the measured population.

5. The thermal imaging system for disease outbreak detection of claim 1, wherein the array of infrared detectors or the central control unit transmit thermal images to an external image processor, then the central control unit receives from the external image processor the temperatures of the individuals in the measured population.

6. The thermal imaging system for disease outbreak detection of claim 1, wherein the system is capable of identifying and tracking the individuals in the measured population temperature distribution likely exhibiting a fever.

7. A method of detecting a fever-causing disease outbreak with the system of claim 1, comprising:
   measuring the temperatures of the individuals the measured population using the array of infrared detectors;
   receiving via an internet connection the temperatures at the central control unit;
   processing the temperatures to form the measured population temperature distribution;
   generating the predicted population temperature distribution;
   comparing the measured population temperature distribution to the predicted population temperature distribution to determine an outbreak condition; and
   issuing an alert when the outbreak condition meets an alert criterion.

8. The method of claim 7, further comprising identifying and tracking the individuals likely exhibiting a fever.

* * * * *